United States Patent
Li et al.

(10) Patent No.: US 9,848,649 B2
(45) Date of Patent: Dec. 26, 2017

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Xingbing Zou, Shenzhen (CN); Long Cai, Shenzhen (CN); Hongxing Duan, Shenzhen (CN); Lizhou Shen, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 268 days.

(21) Appl. No.: 14/673,566

(22) Filed: Mar. 30, 2015

(65) Prior Publication Data

US 2015/0282529 A1     Oct. 8, 2015

(30) Foreign Application Priority Data

Apr. 8, 2014   (CN) ............... 2014 2 0166373 U
Jun. 27, 2014  (CN) ............... 2014 2 0348724 U
Jul. 8, 2014   (CN) ............... 2014 2 0372002 U

(51) Int. Cl.
    *A24F 47/00*     (2006.01)
    *A61M 15/06*     (2006.01)
    *A61M 11/04*     (2006.01)
    *A61M 15/00*     (2006.01)

(52) U.S. Cl.
    CPC ......... *A24F 47/008* (2013.01); *A61M 11/042* (2014.02); *A61M 15/004* (2014.02); *A61M 15/06* (2013.01); *A61M 2205/3653* (2013.01); *A61M 2205/8206* (2013.01)

(58) Field of Classification Search
    CPC ............. A24F 47/008; A61M 15/0031; A61M 15/0036; A61M 15/004; A61M 15/0041
    See application file for complete search history.

(56) References Cited

U.S. PATENT DOCUMENTS

| | | | | |
|---|---|---|---|---|
| 2011/0277760 A1* | 11/2011 | Terry | ............ | A24F 47/008 128/203.12 |
| 2012/0199663 A1* | 8/2012 | Qiu | ............ | A61M 11/041 239/8 |
| 2013/0180533 A1* | 7/2013 | Kim | ............ | A24F 47/008 131/273 |
| 2014/0190477 A1* | 7/2014 | Qiu | ............ | A61M 11/042 128/202.21 |
| 2014/0360514 A1* | 12/2014 | Zhu | ............ | A24F 47/008 131/329 |
| 2015/0040929 A1* | 2/2015 | Hon | ............ | A24F 47/008 131/329 |

* cited by examiner

*Primary Examiner* — Eric Yaary
(74) *Attorney, Agent, or Firm* — Cheng-Ju Chiang

(57) ABSTRACT

An exemplary atomizer includes a liquid supply component, an atomizing assembly, and a pricking means. The liquid supply component is configured for storing tobacco liquid. The liquid supply component has a sealing means for sealing the tobacco liquid therein. The pricking means for pricking the sealing structure so that the tobacco liquid flows to the atomizing assembly. The atomizing assembly is configured for heating the tobacco liquid to form aerosol.

19 Claims, 17 Drawing Sheets

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

Nowadays, electronic cigarettes mainly include disposable electronic cigarettes and refillable electronic cigarette. The disposable electronic cigarettes are not environmental-friendly because they are discarded after used. The refillable electronic cigarettes can be used repeatedly. After tobacco liquid in the refillable electronic cigarettes is used up, the user of the electronic cigarettes can refill the tobacco liquid by themselves. Accordingly, the refillable electronic cigarettes are more environmental-friendly. However, it is inconvenient to refill the tobacco liquid, and the tobacco liquid may pollute clothes of the users during this process.

What is needed, therefore, is an atomizer and an electronic cigarette using same, which can overcome the above shortcomings.

SUMMARY

An exemplary atomizer includes a liquid supply component, an atomizing assembly, and a pricking means. The liquid supply component is configured for storing tobacco liquid. The liquid supply component has a sealing means for sealing the tobacco liquid therein. The pricking means for pricking the sealing structure so that the tobacco liquid flows to the atomizing assembly. The atomizing assembly is configured for heating the tobacco liquid to form aerosol.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
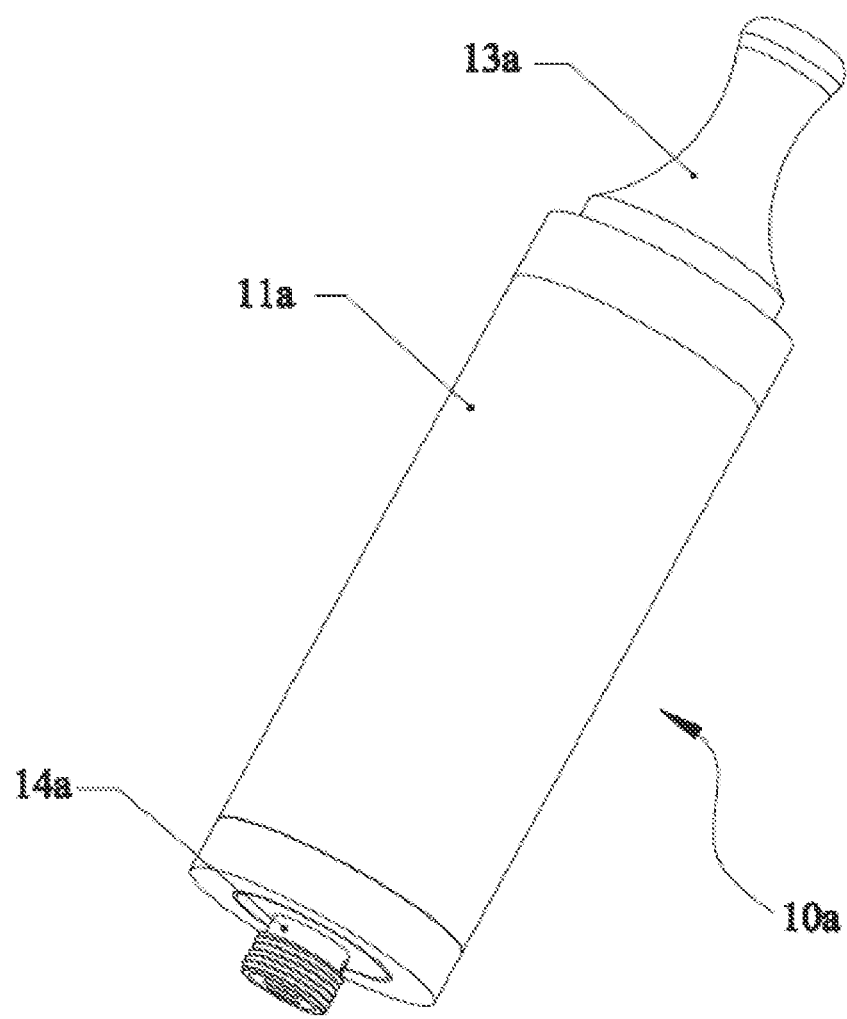
FIG. 1 is a perspective view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
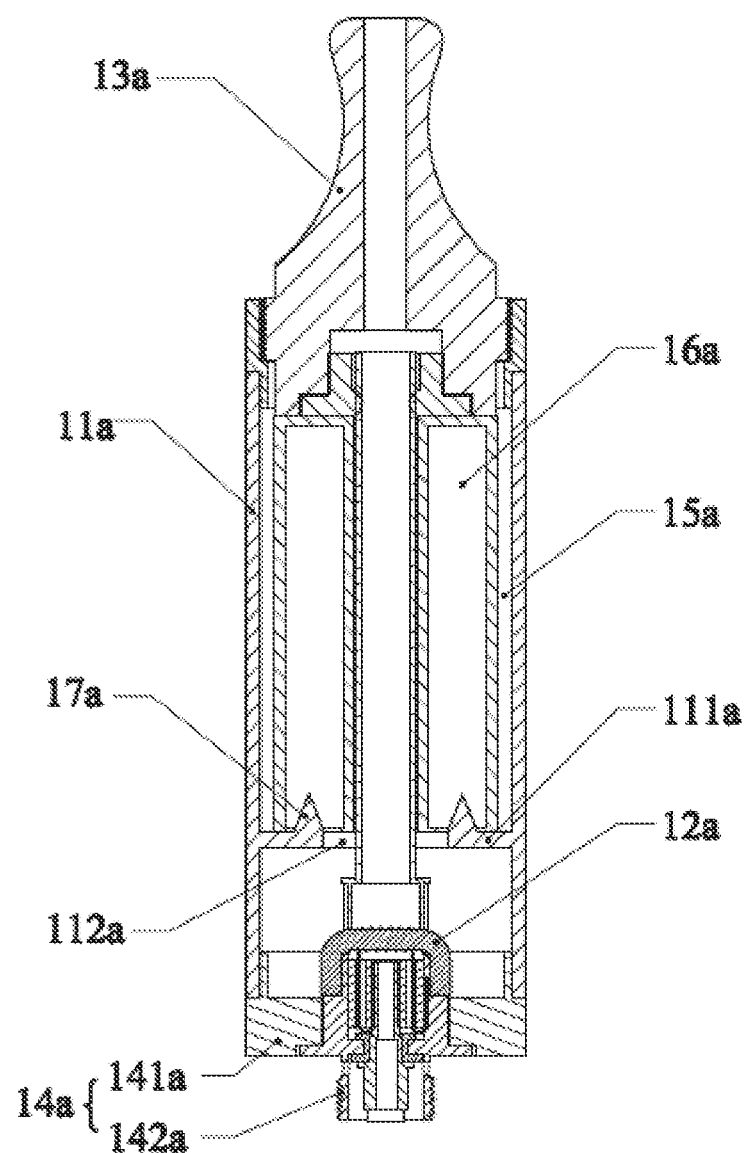
FIG. 2 is a cross-sectional view of the atomizer of FIG. 1.

Referring to FIGS. 1-2, an atomizer 10a according to a first embodiment is shown. The atomizer 10a includes a shell 11a, an atomizing assembly 12a, a mouthpiece 13a at one end of the shell 11a, and an electrical connector 14a. The shell 11a, the mouthpiece 13a and the electrical connector 14a cooperatively define an accommodating space 15a for receiving a liquid supply component 16a. The liquid supply component 16a is detachably arranged in the accommodating space 15a, and is replaceable. The liquid supply component 16a includes a sealing structure 161a at one end. The sealing structure 161a is configured (i.e., structured and arranged) for sealing tobacco liquid in the liquid supply component 16a. The sealing structure 161a may be a hot melt plastic film, a silicone film, or a tin foil. A pricking means is further provided in the accommodating space 15a. When the liquid supply component 16a is pushed into the accommodating space 15a, the pricking means pierces the sealing structure 161a, and the tobacco liquid in the liquid supply component 16a flows out to the atomizing assembly 12a.

The mouthpiece 13a and the shell 11a are detachably connected, e.g., threadedly. The atomizing assembly 12a is arranged at one end adjacent to the electrical connector 14a. Therefore, when the mouthpiece 13a is detached, the liquid supply component 16a can be taken out or placed in from one end of the shell 11a. A circular partition plate 111a is provided on an inner surface of the shell 11a. In the present embodiment, the pricking means includes a plurality of pricking pins 17a arranged on the partition plate 111a. The partition plate 111a defines a liquid inlet 112a. The liquid supply component 16a and the atomizing assembly 12a are arranged on two opposite sides of the partition plate 111a. The tobacco liquid can flow to the atomizing assembly 12a via the liquid inlet 112a.

In the present embodiment, the electrical connector 14a includes a connecting sleeve 141a, and a tubular electrode 142a coaxially arranged with the connecting sleeve 141a. The connecting sleeve 141a is insulated from the tubular electrode 142a. The connecting sleeve 141a is configured for fixedly connecting the shell 11a, and supporting the tubular electrode 142a. The atomizing assembly 12a includes a heating wire 121a, and two ends of the heating wire 121a are respectively connected to the connecting sleeve 141a and the tubular electrode 142a. The connecting sleeve 141a and the tubular electrode 142a are electrically connected to other components for power.

In use, when replacing the liquid supply component 16a, the mouthpiece 13a is screwed off, the liquid supply component 16a is taken out, and a new liquid supply component 16a is placed into the shell 11a. The mouthpiece 13a is screwed on, the liquid supply component 16a is driven to move downwards, and then the pricking pins 17a pierce the sealing structure 161a, so that the tobacco liquid flows to the atomizing assembly 12a via the liquid inlet 112a. When the atomizer 10a is connected to a power supply device, the atomizing assembly 12a heats the tobacco liquid to form aerosol.

Figure 3:
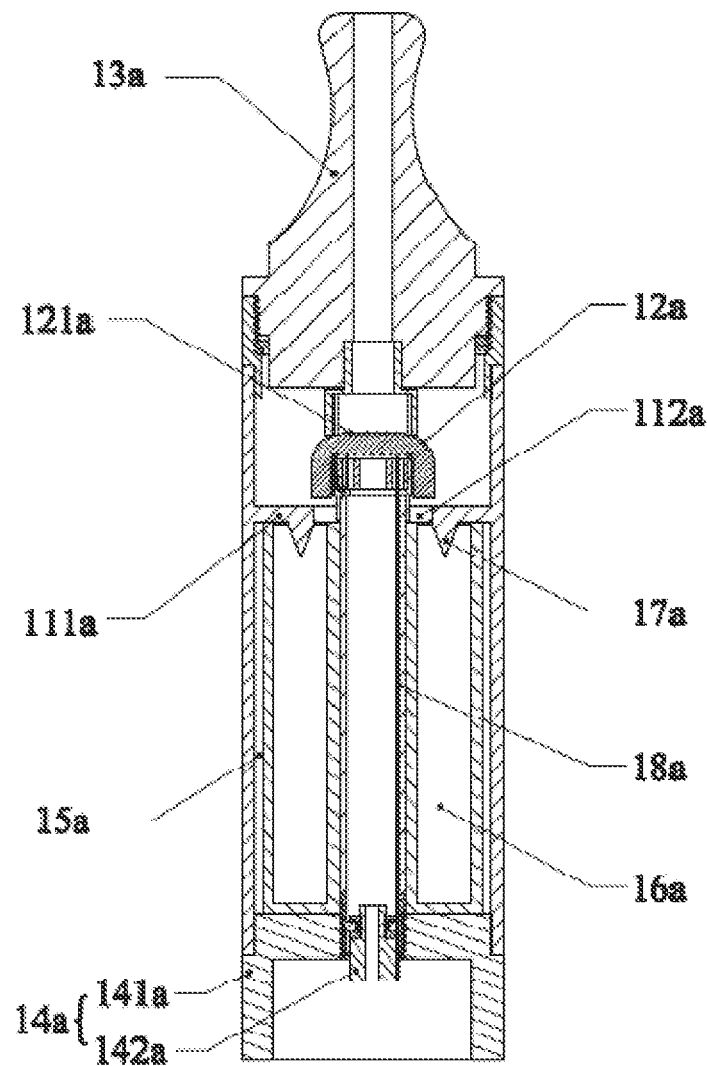
FIG. 3 is a cross-sectional view of an atomizer according to a second embodiment.

Referring to FIG. 3, the atomizer 10a according to a second embodiment is shown. The atomizer 10a includes an air pipe 18a. The connecting sleeve 141a defines a connecting hole 1411a, and an end of the air pipe 18a is detachably engaged in the connecting hole 1411a. The atomizer 10a is substantially similar to that of FIGS. 1-2, except that the position of the atomizing assembly 12a and the engagement between the air pipe 18a and the connecting sleeve 141a. The atomizing assembly 12a is supported by the air pipe 18a, and is positioned between the mouthpiece 13a and the liquid supply component 16a. The connecting sleeve 141a is threadedly coupled with the air pipe 18a. In use, the connecting sleeve 141a is screwed off, the liquid supply component 16a is assembled into the accommodating space 15a, and then the connecting sleeve 141a is engaged with the air pipe 18a threadedly.

Figure 4:
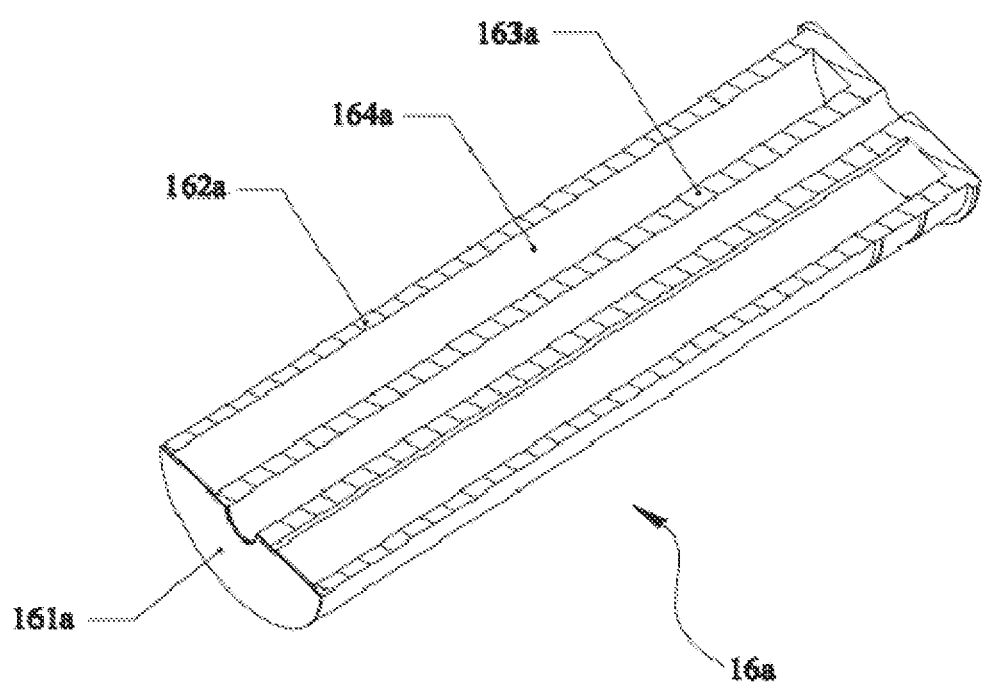
FIG. 4 is a cross-sectional view of a liquid supply component in FIGS. 2-3.

Referring to FIG. 4, the liquid supply component 16a includes an inner tube 163a and an outer tube 162a nesting the inner tube 163a. The outer tube 162a and the inner tube 163a cooperatively define an annular liquid storage chamber 164a. A first end of the liquid storage chamber 164a is closed, and an opposite second end of the liquid storage chamber 164a is sealed by the sealing structure 161a. Tobacco liquid is sealed in the liquid storage chamber 164a. In use, the liquid supply component 16a is received in the 16a in such a manner that the inner tube 163a nests the air pipe 18a. Accordingly, it is very convenient to assemble and replace the liquid supply component 16a.

Figure 5:
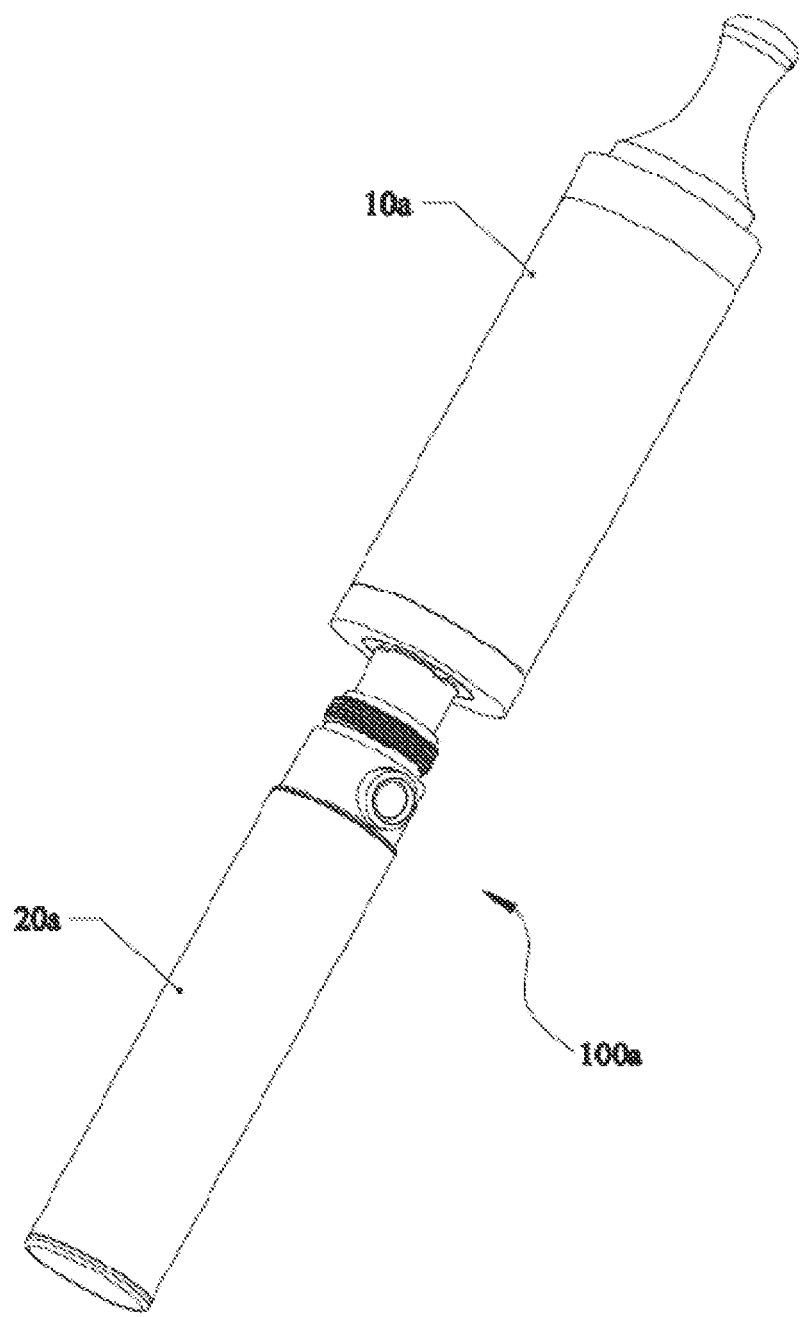
FIG. 5 is a perspective view of an electronic cigarette according to a third embodiment.

Referring to FIG. 5, an electronic cigarette 100a according to a third embodiment is shown. The electronic cigarette 100a includes the atomizer 10a and a power supply 20a. The atomizer 10a is configured for heating the tobacco liquid to form aerosol. The power supply 20a is adapted for supplying the atomizer 220a power.

Figure 6:
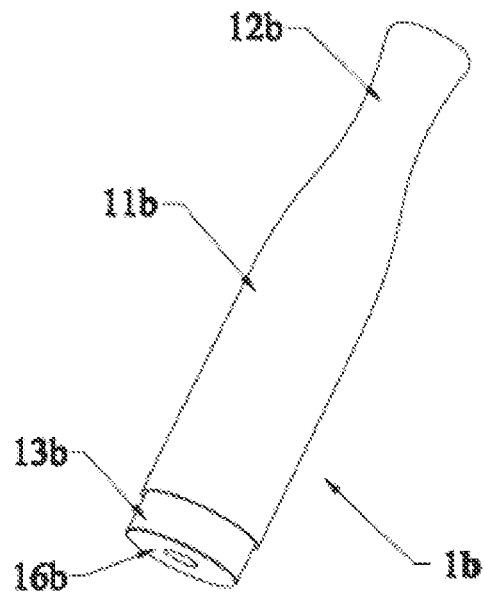
FIG. 6 is a perspective view of a liquid supply component according to a fourth embodiment.
Figure 7:
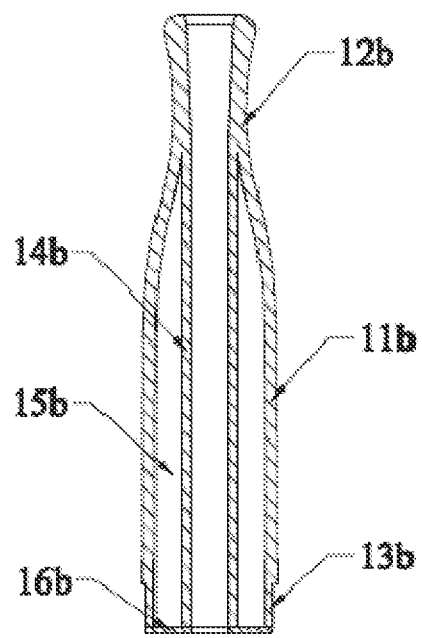
FIG. 7 is a cross-sectional view of the liquid supply component of FIG. 6.

Referring to FIGS. 6-7, a liquid supply component 1b according to a fourth embodiment. The liquid supply component 1b includes a mouthpiece 12b at one end, a shell 11b, and an air pipe 14b extending from the mouthpiece 12b. The shell 11b nests the air pipe 14b. The air pipe 14b and the shell 11b cooperatively form an annular liquid storage chamber 15b. The liquid storage chamber 15b defines an opening. A sealing structure 16b is provided at the opening, and is configured for sealing tobacco liquid in the liquid storage chamber 15b. The sealing structure 16b may be a plastic film or a silicone film.

The liquid supply component 1b further includes an engaging part 13b at one end of the shell 11b. The engaging part 13b and the shell 11b are integrally formed.

Figure 8:
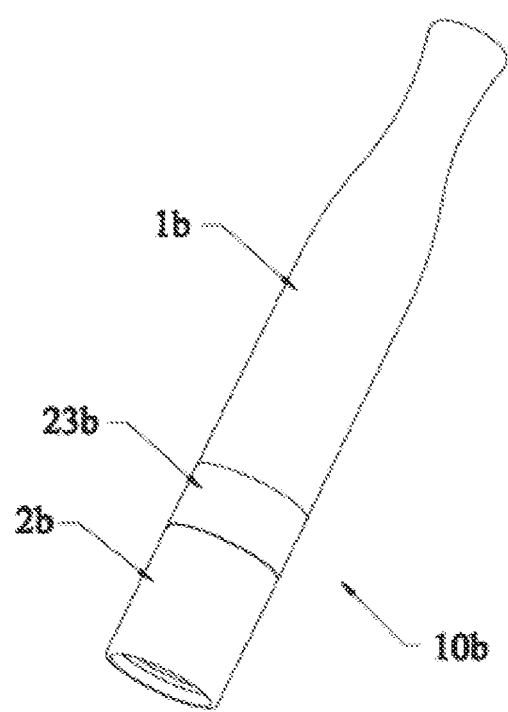
FIG. 8 is a perspective view of an atomizer according to a fifth embodiment.
Figure 9:
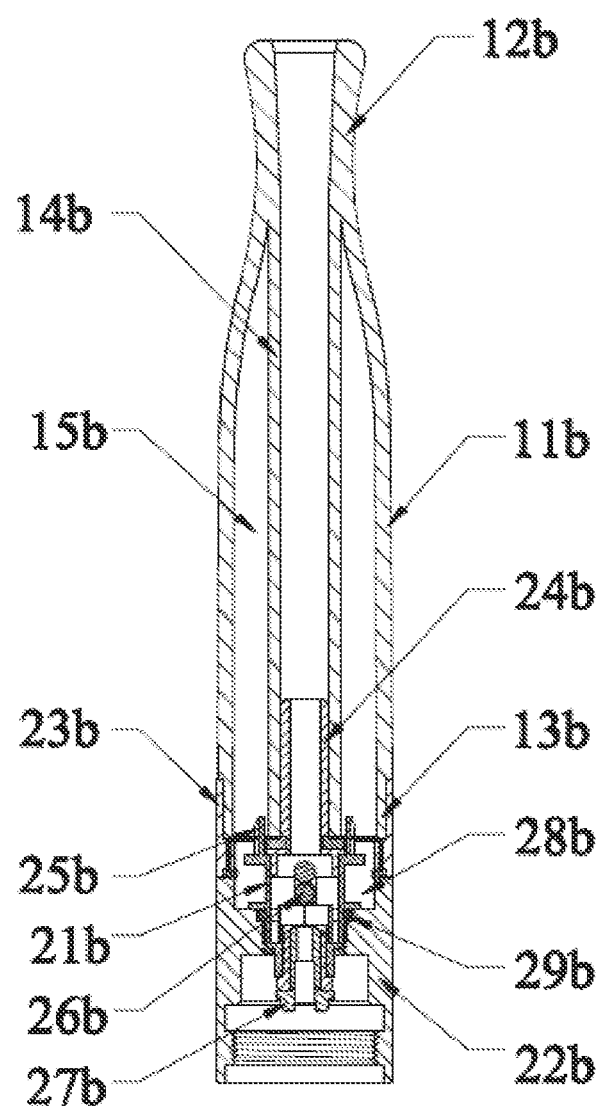
FIG. 9 is a cross-sectional view of the atomizer of FIG. 8.
Figure 10:
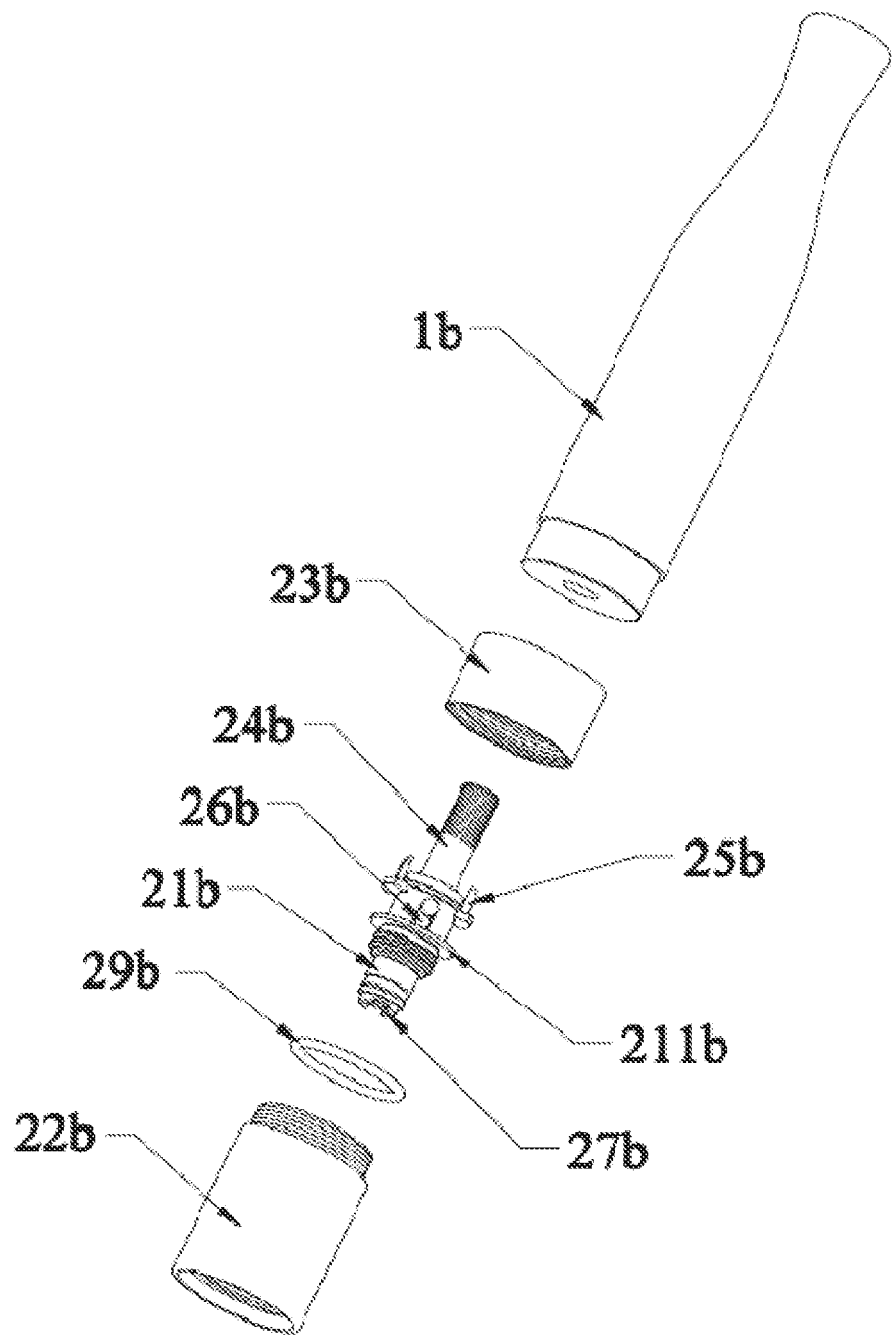
FIG. 10 is an exploded perspective view of the atomizer of FIG. 8.

Referring to FIGS. 8-10, an atomizer 10b according to a fifth embodiment is shown. The atomizer 10b includes the liquid supply component 1b and an atomizing head 2b detachably connected with the liquid supply component 1b. The atomizing head 2b is configured for absorbing and heating tobacco liquid to form aerosol.

The atomizing head 2b includes a connecting element 23b, an air conducting pipe 24b, a pricking means 25b, an atomizing assembly 26b, a holder 21b, a fixing sleeve 22b, and a tubular electrode 27b. The connecting element 23b is configured for coupling with the engaging part 13b. The air conducting pipe 24b is configured to insert into the air pipe 14b. The pricking means 25b is configured to insert into the liquid storage chamber 15b, thus allowing tobacco liquid flowing out of the liquid storage chamber 15b. The atomizing assembly 26b is configured for absorbing and heating the tobacco liquid. The holder 21b is configured to fasten the air conducting pipe 24b, the pricking means 25b, and the atomizing assembly 26b. The tubular electrode 27b is arranged in the holder 21b. The fixing sleeve 22b is configured to fixedly connect with an external component. The fixing sleeve 22b is electrically conductive, and insulated from the tubular electrode 27b. Two opposite ends of the atomizing assembly 26b are connected to the tubular electrode 27b and the fixing sleeve 22b, respectively. The engaging part 13b is coupled to the connecting element 23b by interference fit. The connecting element 23b and the fixing sleeve 22b are engaged by screw threads.

The holder 21b is threadedly fixed in the fixing sleeve 22b. The holder 21b and the fixing sleeve 22b cooperatively form an atomizing cavity 28b, and the atomizing assembly 26b is fixed by the holder 21b, and is positioned in the atomizing cavity 28b.

In the present embodiment, a sealing ring 29b is further provided between the holder 21b and the fixing sleeve 22b to prevent tobacco liquid from leaking. The holder 21b further includes a flange 211b shielding the sealing ring 29b.

Figure 11:
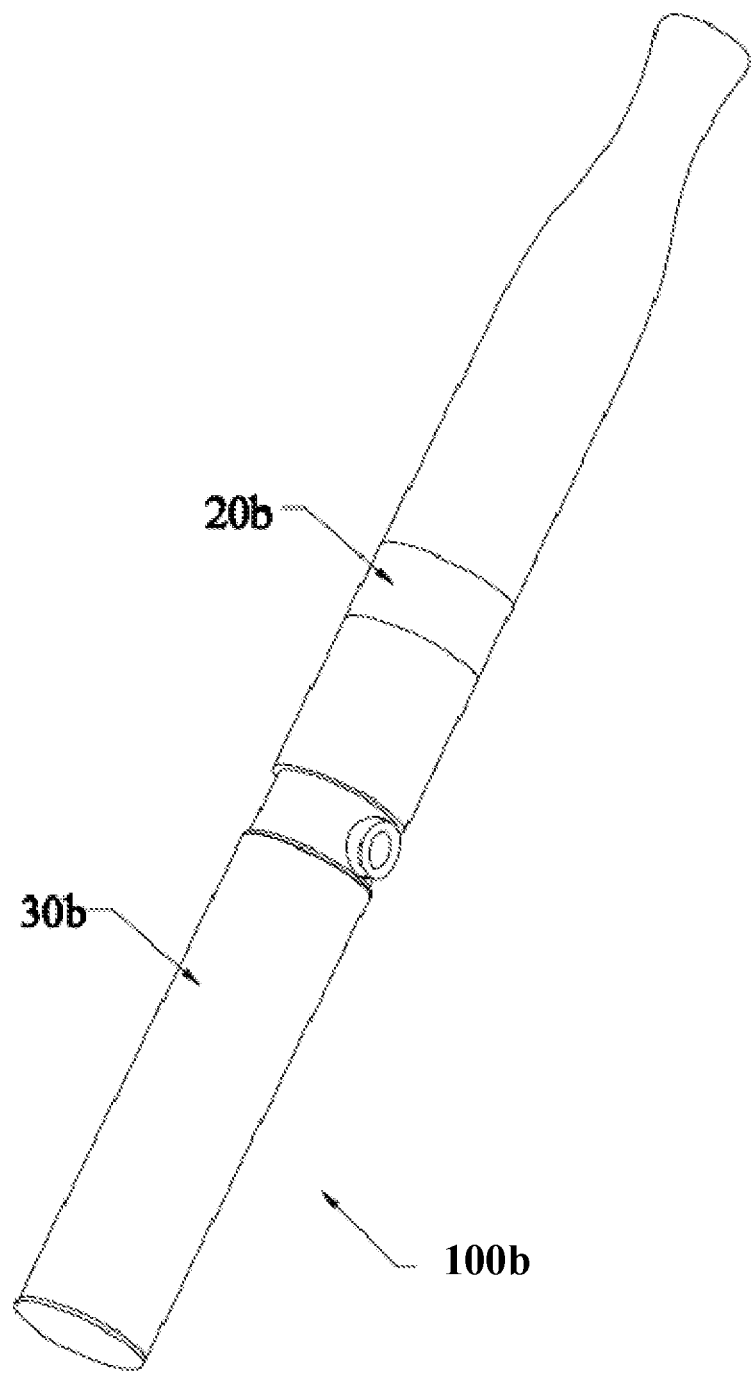
FIG. 11 is a perspective view of an electronic cigarette according to a sixth embodiment.

Referring to FIG. 11, an electronic cigarette 100b according to a sixth embodiment is shown. The electronic cigarette 100b includes the atomizer 20b and a power supply 30b connected with the atomizer 20b.

Figure 12:
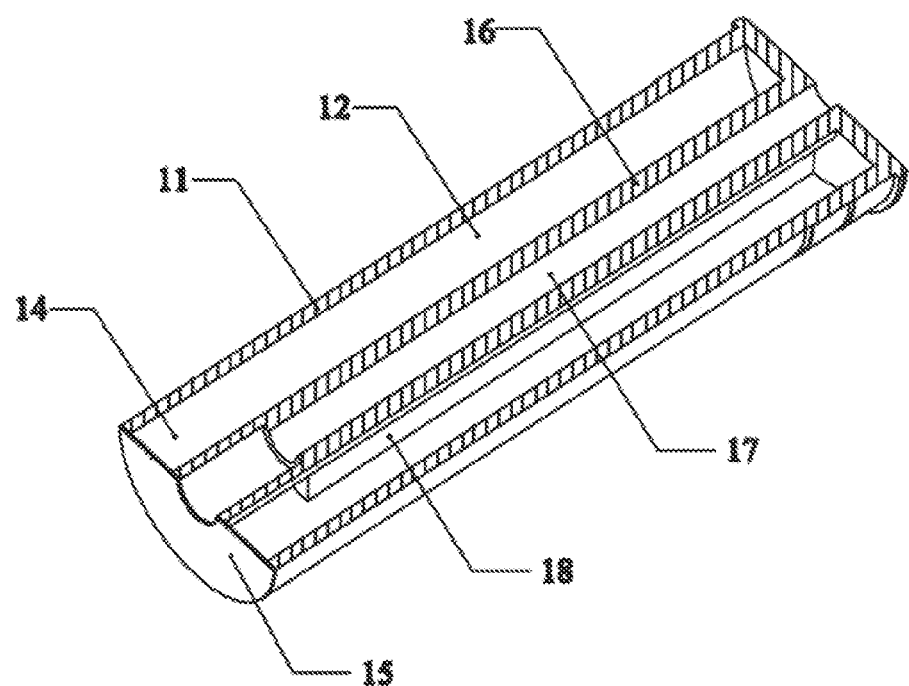
FIG. 12 is a perspective cut-off view of a liquid supply component according to a seventh embodiment.
Figure 13:
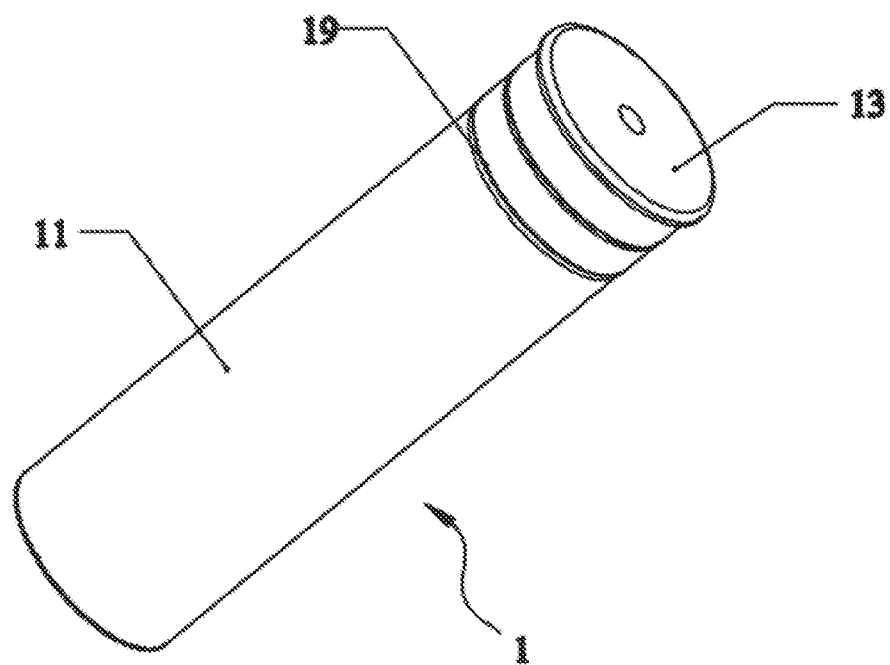
FIG. 13 is a perspective view of the liquid supply component of FIG. 12.
Figure 14:
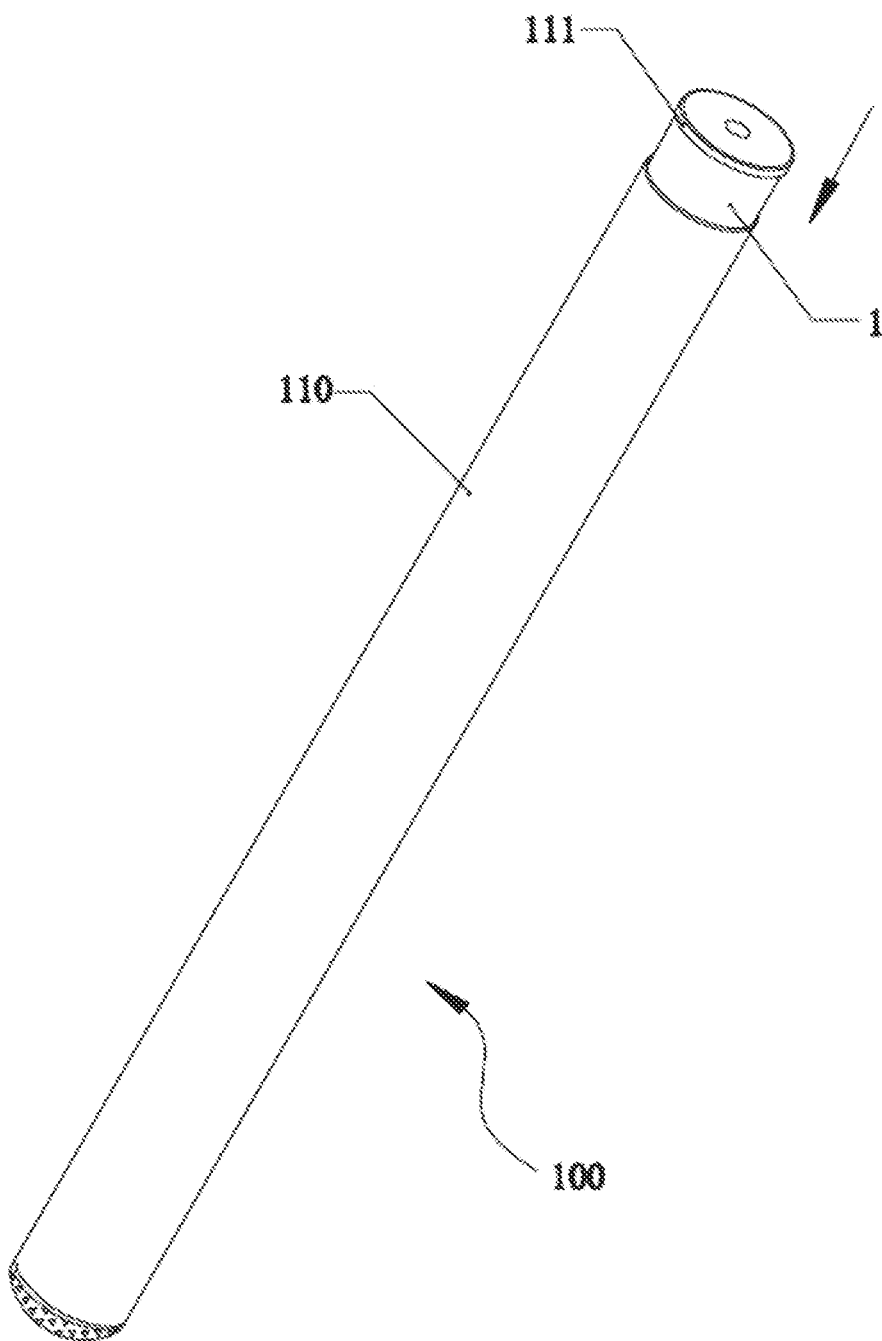
FIG. 14 is a perspective view of an electronic cigarette according to an eighth embodiment.
Figure 15:
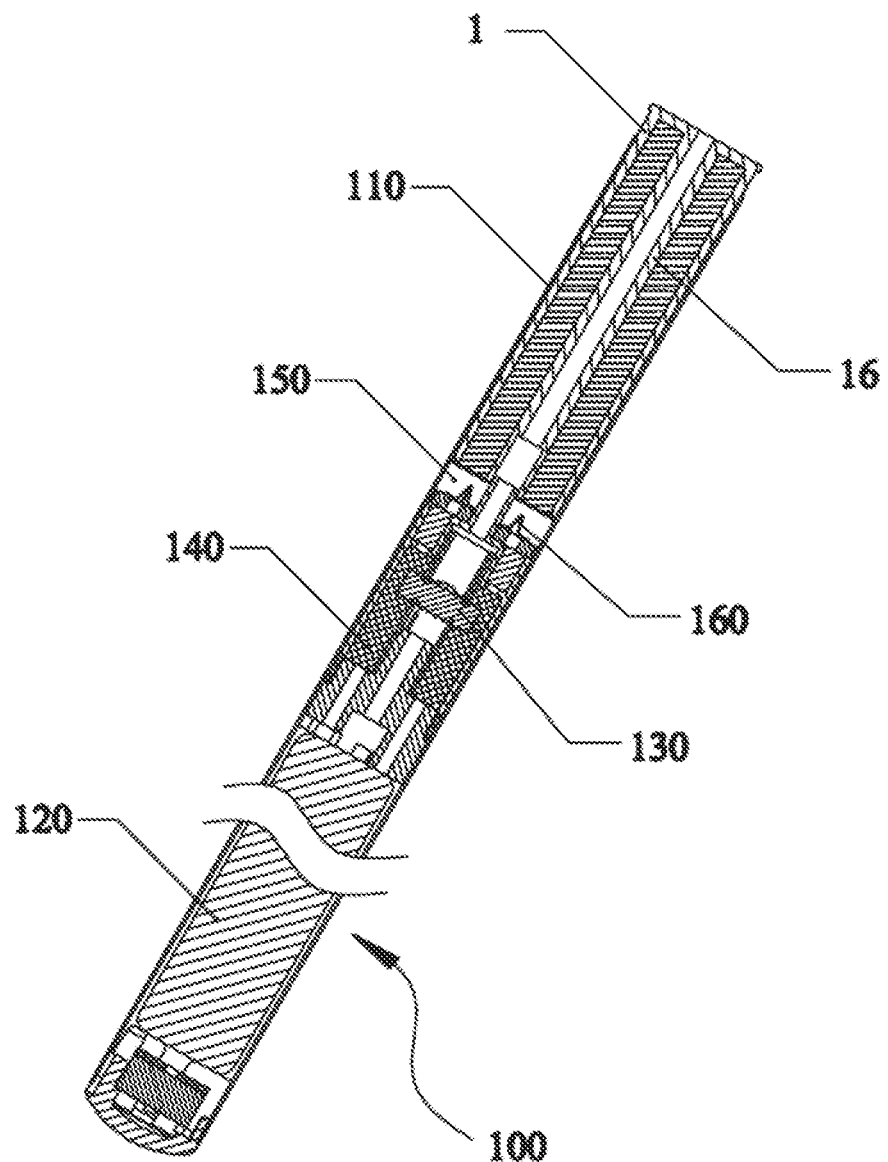
FIG. 15 is a cross-sectional view of the electronic cigarette of FIG. 14.
Figure 16:
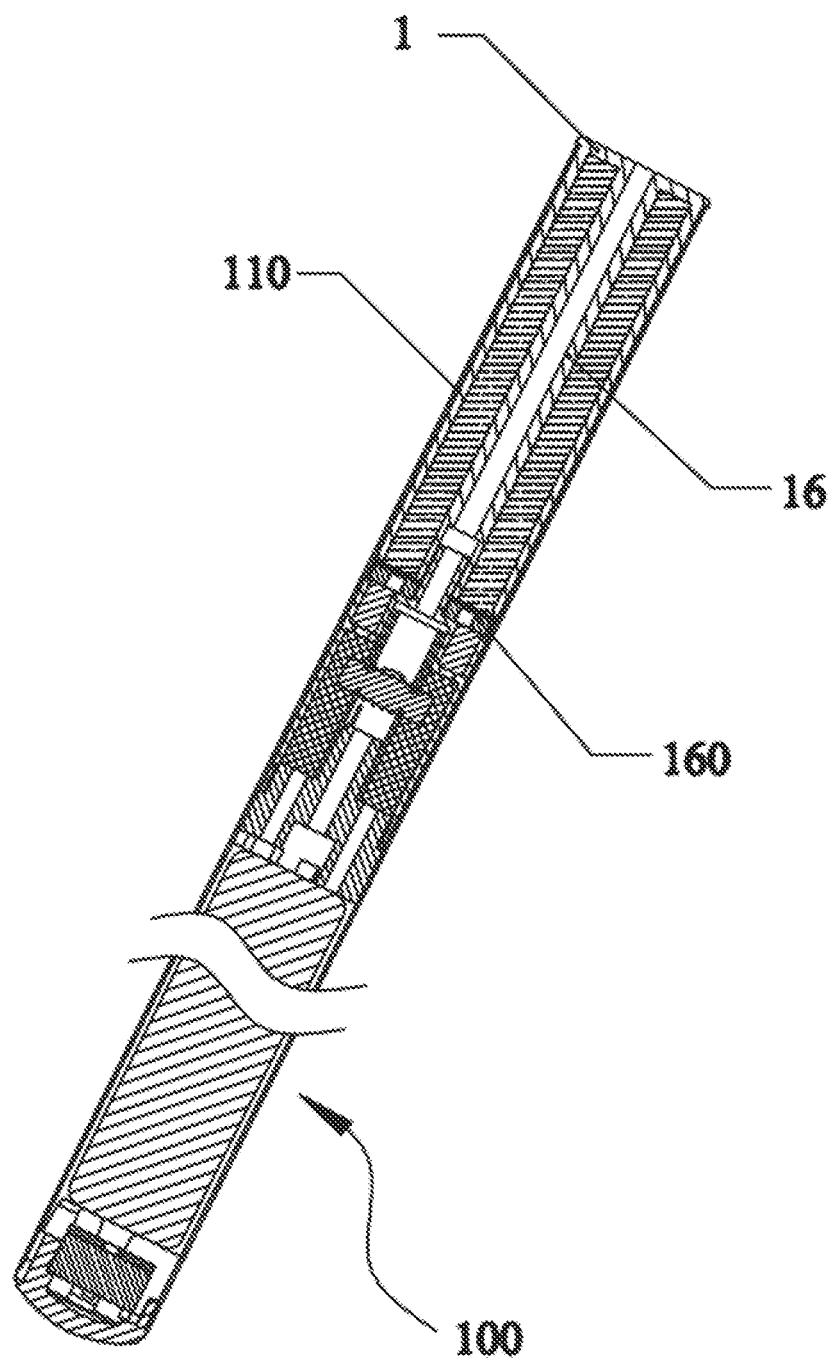
FIG. 16 is a cross-sectional view of the electronic cigarette in a working state of FIG. 14.
Figure 17:
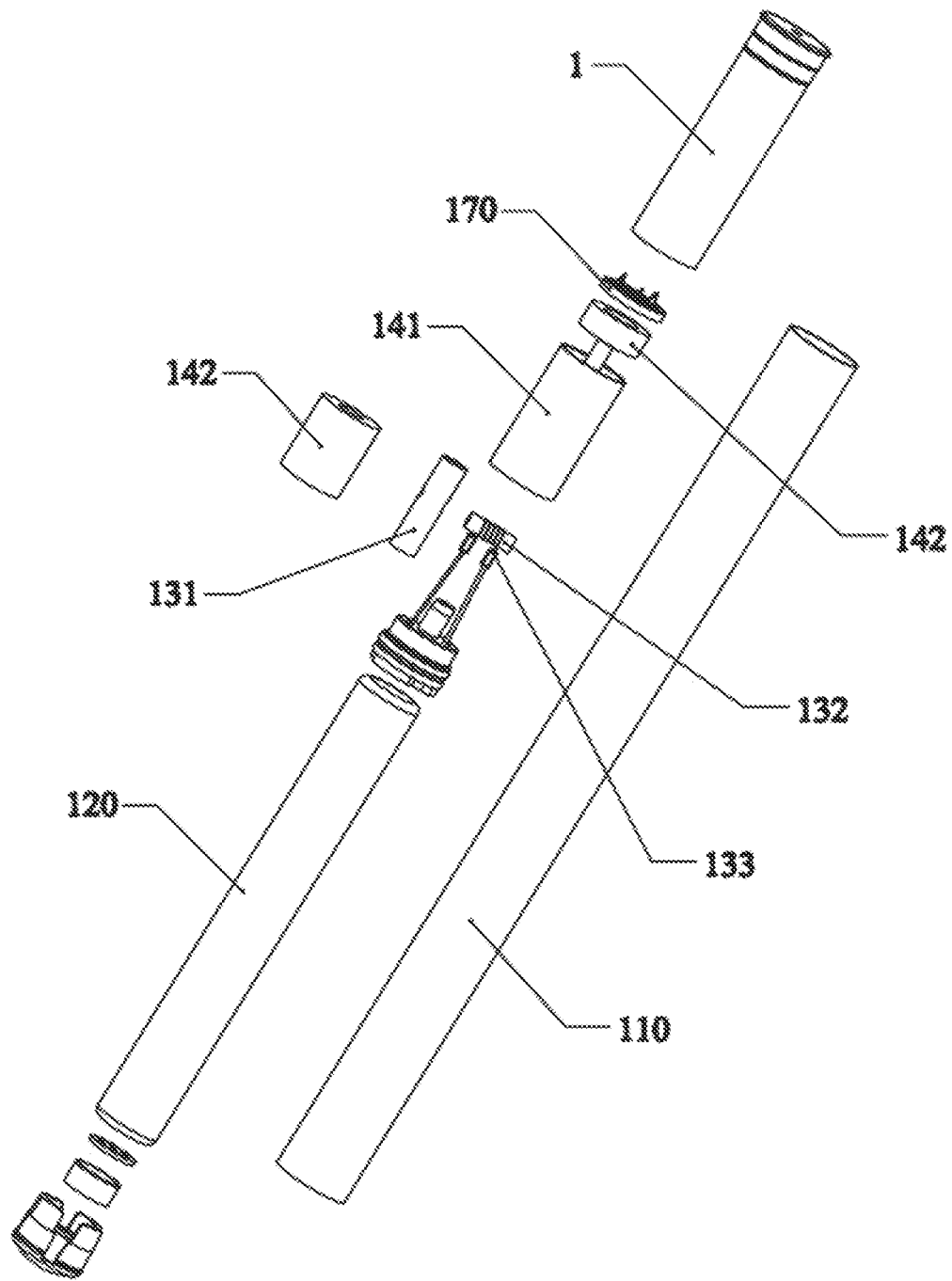
FIG. 17 is an exploded perspective view of the electronic cigarette of FIG. 14.
Figure 18:
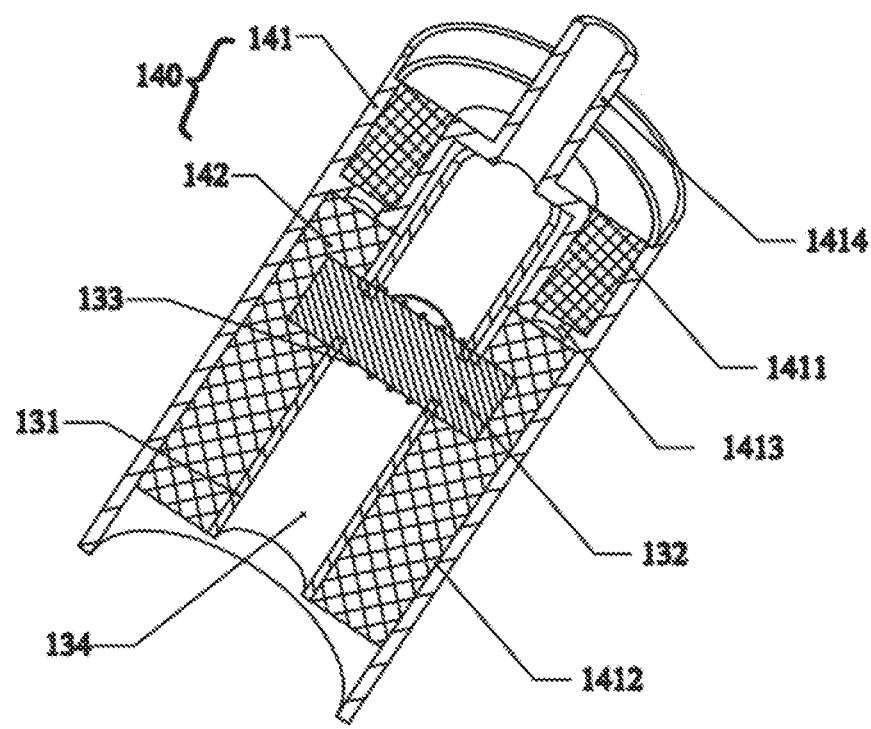
FIG. 18 is a perspective cut-off view of a liquid absorbing component in the electronic cigarette of FIG. 14.

Referring to FIGS. 12-13, a liquid supply component 1 for an electronic cigarette is provided. The liquid supply component 1 is configured (i.e., structured and arranged) for storing tobacco liquid. The liquid supply component 1 includes a cylindrical shell 11 defining a liquid storage chamber 12. The shell 11 includes an end wall 13 at one end, and an opening 14 at the other end. The end wall 13 is configured for sealing the liquid storage chamber 12. A sealing structure 15 is provided at the opening 14 to seal the liquid storage chamber 12. An air pipe 16 is provided in the liquid storage chamber 12, and is oriented along an axis of the shell 11. The air pipe 16 extends from the end wall 13 to the opening 14. An annular liquid storage space is defined between the air pipe 16 and the shell 11.

The air pipe 16 defines an air passage 17 extending through the end wall 13 to form a mouthpiece. In the present embodiment, the air pipe 16 and the shell 11 are coaxially arranged. Further, a rib plate 18 is provided around the air pipe 16, and is configured for supporting the air pipe 16.

Before filling the tobacco liquid, one end of the liquid supply component 1 is open. After filling the tobacco liquid into the liquid storage chamber 12 between the shell 11 and the air pipe 16, the sealing structure 15 is used to seal the opening 14 of the shell 11. For easy production, the sealing structure 15 may be a thin film, for example, a hot melt adhesive membrane. The sealing structure 15 is pressed onto one end of the shell 11 and the air pipe 16, and is heated so as to firmly adhere to the shell 11 and the air pipe 16. In this way, the tobacco liquid is sealed in the liquid storage chamber 12.

In use, the liquid supply component 1 is assembled into an electronic cigarette (described in detail later). To prevent the slippage of the liquid supply component 1 during use, an anti-slip structure is provided on an external surface of the shell 11, and the shell and a housing of the electronic cigarette is coupled by interference fit.

Referring to FIGS. 14-18, an electronic cigarette 100 is shown. The electronic cigarette 100 includes a housing 110, a power supply 120, an atomizing assembly 130, and a liquid absorbing component 140. The liquid supply component 1 is arranged at one end of the housing 110. One part of the shell 11 of the liquid supply component 1 is positioned in the housing 110, and is engaged with the housing 110 by interference fit. The other part of the shell 11 exposes from the housing 110. A space 150 is provided between the liquid supply component 1 and the liquid absorbing component 140. The space 150 is for receiving the liquid supply component 1 when the liquid supply component 1 is pushed into the housing 110. A plurality of pricking pins 160 are provided in the space 150. The pricking pins 160 are configured for inserting into an end of the liquid supply component 1 via the sealing structure 15, so that the tobacco liquid sealed in the liquid supply component 1 flows to the liquid absorbing component 140, and then to the atomizing assembly 130.

In the present embodiment, the housing 110 is integrally formed and is cylindrical. A length of the space 150 in a central axis of the housing 110 is larger than or equal to that of a part of the liquid supply component 1, which protrudes from the housing 110. That is, when the liquid supply component 1 is pushed into the housing 110, the liquid supply component 1 is completely located in the housing 110.

The liquid supply component 1 includes a flange 111 at one end. When the liquid supply component 1 is engaged in the housing 110, the flange 111 abuts against an end of the housing 110. A diameter of the flange is equal to that of the housing 110, so that an outer surface of the flange 111 aligns with that of the housing 110.

The liquid absorbing component 140 is configured for absorbing the tobacco liquid from the liquid supply component 1. The liquid absorbing component 140 includes a frame 141 and a porous body 142 in the frame 141. The porous body 142 is wrapped around the atomizing assembly 130, so that the porous body 142 provides the atomizing assembly 130 the tobacco liquid for atomizing. In the present embodiment, the frame 141 includes a buffer area 1411 adjacent to liquid supply component 1 and a liquid storage area 1412 away from the liquid supply component 1. The porous body 142 is arranged in both of the buffer area 1411 and the liquid storage area 1412. At least one through hole 1413 connects the buffer area 1411 and the liquid storage area 1412. The tobacco liquid flows to the buffer area 1411 from the liquid supply component 1. After the buffer area 1411 absorbs enough tobacco liquid, the tobacco liquid flows to the liquid storage area 1412 via the through hole 1413, is then conveyed to the atomizing assembly 130. The design of the buffer area 1411 and the liquid storage area 1412 can prevent the atomizing assembly 130 from leaking.

The atomizing assembly 130 includes a glass fiber tube 131, and a glass fiber core 132 supported by the glass fiber tube 131, and a heating wire wound around the glass fiber core 132. The tobacco liquid is conveyed to the glass fiber core 132 from the porous body 142 by capillary action, and is then heated to form aerosol by the heating wire 133. The glass fiber tube 131 defines an atomizing cavity 134, and aerosol is expelled from the atomizing cavity 134.

The frame 141 further includes a hollow air guiding rod 1414 protruding therefrom. The air guiding rod 1414 communicates with the atomizing cavity 134, and is capable of inserting into the air pipe 16 of the liquid supply component 1.

Figure 19:
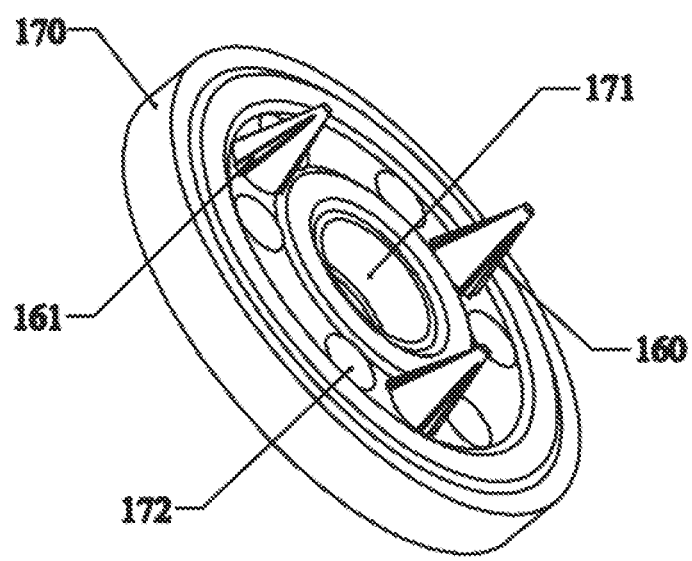
FIG. 19 is a perspective view of a spacer in the electronic cigarette of FIG. 14.

Referring to FIG. 19, in the present embodiment, the pricking pins 160 are arranged on a spacer 170. The spacer 170 nests the air guiding rod 1414. The spacer 170 is coaxially arranged with the liquid supply component 1. The spacer 170 is annular shaped, and defines a central hole 171. The pricking pins 160 are arranged around the central hole 171. The spacer 170 further defines a plurality of holes 172 adjacent to the pricking pins 160. The holes 172 allow the tobacco liquid to flow into the liquid absorbing component 140. Further, the pricking pins 160 define one or more grooves 161 for facilitating the flow of the tobacco liquid. In other embodiments, the pricking pins 160 may be hollow, so that the tobacco liquid may flow into the liquid absorbing component 140 by passing through the pricking pins 160.

Figure 20:
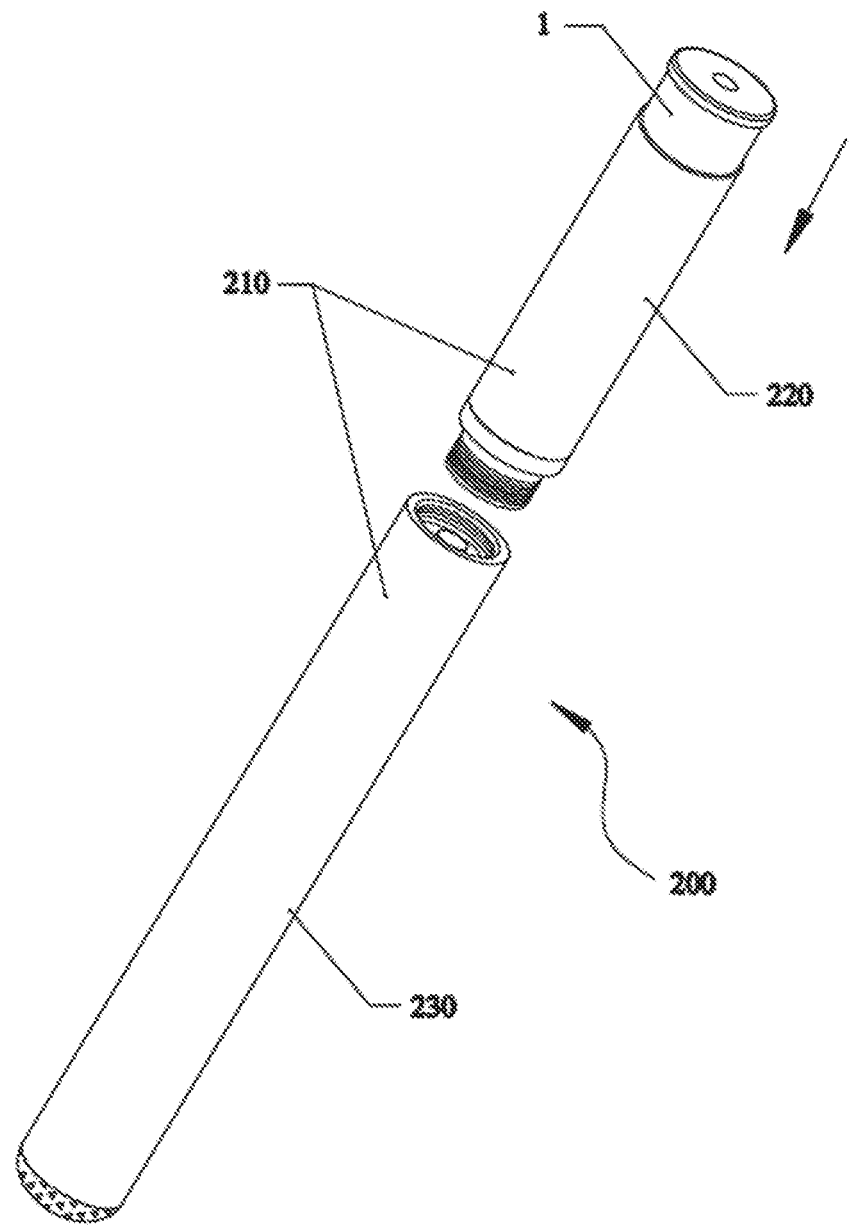
FIG. 20 is a perspective view an electronic cigarette according to a ninth embodiment.

Referring to FIG. 20, another electronic cigarette 200 is shown. The electronic cigarette 200 includes a housing 210. The housing 210 has a first part for receiving an atomizer 220, and a second part for accommodating a battery rod 230. The atomizer 220 is atomizing tobacco liquid, and the battery rod 230 is adapted for supplying the atomizer 220 power. The atomizer 220 is detachably connected to the battery rod 230, for example, threadedly.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An electronic cigarette comprising an atomizer and a power supply configured for providing the atomizer power, the atomizer comprising:
   a liquid supply component, the liquid supply component being configured for storing tobacco liquid, the liquid supply component having a sealing means for sealing the tobacco liquid therein;
   an atomizing assembly; and
   a pricking means for pricking the sealing means so that the tobacco liquid flows to the atomizing assembly, the pricking means comprising an annular shaped plate located between the liquid supply component and the atomizing assembly, a plurality of pricking pins extending from the plate toward the liquid supply component and a plurality of holes disposed in the plate beside the plurality of pricking pins, the plurality of holes and the plurality of pricking pins being all distributed around a central axis of the plate, the atomizing assembly configured for heating the tobacco liquid to form aerosol.

2. The electronic cigarette of claim 1, further comprising:
   a shell, the atomizer being arranged in the shell;
   a mouthpiece at a first end of the shell; and
   an electrical connector at an opposite second end of the shell, wherein the shell, the mouthpiece, and the electrical connector cooperatively define an accommodating space, the liquid supply component is detachably received in the accommodating space, and the pricking means is received in the accommodating space.

3. The electronic cigarette of claim 2, wherein the mouthpiece is detachably connected with the shell, and the liquid supply component is arranged between the mouthpiece and the atomizing assembly.

4. The electronic cigarette of claim 3, wherein the shell comprises a circular partition plate provided on an inner surface of the shell to perform as the pricking means, the partition plate defines a liquid inlet, and the tobacco liquid flows to the atomizing assembly via the liquid inlet.

5. The electronic cigarette of claim 2, further comprising an air pipe, wherein the atomizing assembly is supported by a first end of the air pipe, and is arranged between the mouthpiece and the liquid supply component; the electrical connector comprises a connecting sleeve, the connecting sleeve defines a connecting hole, and an opposite second end of the air pipe is detachably engaged in the connecting hole.

6. The electronic cigarette of claim 5, wherein the shell comprises a circular partition plate provided on an inner surface of the shell to perform as the pricking means, the partition plate defines a liquid inlet, and the tobacco liquid flows to the atomizing assembly via the liquid inlet.

7. The electronic cigarette of claim 1, wherein the liquid supply component comprises a mouthpiece at one end, a shell extending from the mouthpiece, and an air pipe extending from the mouthpiece; the shell nests the air pipe, the shell is coaxially arranged with the air pipe, the air pipe and the shell cooperatively define an annular liquid storage chamber for storing the tobacco liquid, the liquid storage chamber defines an opening, and the sealing means seals the opening.

8. The electronic cigarette of claim 7, wherein the liquid supply component further comprises an engaging part at an opposite one end of the shell, the engaging part and the shell are integrally formed.

9. The electronic cigarette of claim 8, further comprising:
   a connecting element configured for coupling with the engaging part; and
   an air conducting pipe configured to insert into the air pipe.

10. The electronic cigarette of claim 9, further comprising:
    a holder for fixing the air conducting pipe, the pricking means, the atomizing assembly;
    a fixing sleeve connected to the connecting element; and
    a tubular electrode arranged in the holder, the tubular electrode being electrically insulated from the fixing sleeve.

11. The electronic cigarette of claim 10, wherein the holder is fixed in the fixing sleeve, the holder and the fixing sleeve cooperatively define an atomizing cavity, and the atomizing assembly is fixed by the holder, and is positioned in the atomizing cavity.

12. The electronic cigarette of claim 7, further comprising a rib plate arranged around the air pipe, wherein the rib plate is configured for supporting the air pipe.

13. The electronic cigarette of claim 1, wherein the sealing means is selected from any of the group consisting of a hot melt plastic film, a silicone film, and a tin foil.

14. The electronic cigarette of claim 1, further comprising:
    a housing, the atomizing assembly and the power supply being received in the housing, the liquid supply component being arranged at one end of the housing; and
    a liquid absorbing component received in the housing;
    wherein the liquid absorbing component and a main body of the liquid supply component cooperatively define a space, the pricking means is positioned in the space; a first part of the main body is accommodated in the housing, and a second part of the main body exposes from the housing; when the second part of the main body is pushed into the housing, the pricking means pricks the sealing structure, so that the tobacco liquid flows to the liquid absorbing component, and is then conveyed to the atomizing assembly.

15. The electronic cigarette of claim 14, wherein a length of the space along an axis of the housing is larger than or equal to that of the second part of the main body.

16. The electronic cigarette of claim 14, wherein the liquid absorbing component comprises a frame and a porous body in the frame, and the porous body is wrapped around the atomizing assembly.

17. The electronic cigarette of claim 16, wherein the frame comprises a buffer area adjacent to liquid supply component and a liquid storage area away from the liquid supply component, the porous body is arranged in at least the liquid storage area, at least one through hole formed in the frame connects the buffer area and the liquid storage area.

18. An atomizer, comprising:
    a liquid supply component, the liquid supply component being configured for storing tobacco liquid, the liquid supply component having a sealing means for sealing the tobacco liquid therein;
    an atomizing assembly; and
    a pricking means for pricking the sealing means so that the tobacco liquid flows to the atomizing assembly, the atomizing assembly configured for heating the tobacco liquid to form aerosol;
    a shell, the atomizer being arranged in the shell;
    a mouthpiece at a first end of the shell; and
    an electrical connector at an opposite second end of the shell, wherein the shell, the mouthpiece, and the electrical connector cooperatively define an accommodating space, the liquid supply component is detachably received in the accommodating space, and the pricking means is received in the accommodating space; and an air pipe, wherein the atomizing assembly is supported by a first end of the air pipe, and is arranged between the mouthpiece and the liquid supply component; the electrical connector comprises a connecting sleeve, the connecting sleeve defines a connecting hole, and an opposite second end of the air pipe is detachably engaged in the connecting hole.

19. The atomizer of claim 18, wherein the shell comprises a circular partition plate provided on an inner surface of the shell, the pricking means comprises a plurality of pricking pins arranged on the partition plate, the partition plate defines a liquid inlet, the liquid supply component and the atomizing assembly are arranged on two opposite sides of the partition plate, and the tobacco liquid flows to the atomizing assembly via the liquid inlet.

* * * * *